US009033707B2

(12) United States Patent
Dricot

(10) Patent No.: US 9,033,707 B2
(45) Date of Patent: May 19, 2015

(54) METHOD AND TOOL FOR CREATING A PERFORATION OR CAVITY IN A BONE OR BONE STRUCTURE IN CONTACT WITH A MEMBRANE

(76) Inventor: Roland Dricot, Dilbeek (BE)

( * ) Notice: Subject to any disclaimer, the term of this patent is extended or adjusted under 35 U.S.C. 154(b) by 478 days.

(21) Appl. No.: 12/706,209

(22) Filed: Feb. 16, 2010

(65) Prior Publication Data

US 2010/0167233 A1    Jul. 1, 2010

Related U.S. Application Data

(63) Continuation-in-part of application No. 12/666,604, filed as application No. PCT/BE2007/000068 on Jun. 27, 2007, now abandoned.

(51) Int. Cl.
| | |
|---|---|
| *A61C 8/00* | (2006.01) |
| *A61C 1/00* | (2006.01) |
| *A61C 1/12* | (2006.01) |
| *A61C 1/05* | (2006.01) |
| *A61C 1/08* | (2006.01) |

(52) U.S. Cl.
CPC .............. *A61C 1/0061* (2013.01); *A61C 1/055* (2013.01); *A61C 1/087* (2013.01); *A61C 1/12* (2013.01); *A61C 8/0089* (2013.01); *A61C 8/0092* (2013.01)

(58) Field of Classification Search
CPC ..................................................... A61C 8/0092
USPC ......... 433/80, 82, 84, 85, 100, 104, 165, 166, 433/215; 606/79, 80, 90, 92, 93, 94, 95, 606/167, 191; 408/57, 58, 67
See application file for complete search history.

(56) References Cited

U.S. PATENT DOCUMENTS

| | | | | |
|---|---|---|---|---|
| 3,128,079 A | * | 4/1964 | De Groff | 415/123 |
| 3,762,052 A | * | 10/1973 | Melde | 433/120 |
| 4,021,920 A | * | 5/1977 | Kirschner et al. | 433/82 |
| 4,199,160 A | * | 4/1980 | Bent | 279/30 |
| 5,055,043 A | * | 10/1991 | Weiss et al. | 433/86 |
| 5,429,504 A | | 7/1995 | Peltier et al. | |
| 6,579,093 B2 | * | 6/2003 | Bailey et al. | 433/132 |

(Continued)

FOREIGN PATENT DOCUMENTS

| | | |
|---|---|---|
| AT | 504 780 A4 | 8/2008 |
| AT | 504780 B1 * | 8/2008 |

(Continued)

OTHER PUBLICATIONS

English language translation of DE 103 22 869 B3, Nov. 18, 2004.*
English language machine translation for AT504780B1, Aug. 15, 2008.*
English language machine translation of EP1269933A2, Jan. 2, 2003.*

(Continued)

*Primary Examiner* — Ralph Lewis
(74) *Attorney, Agent, or Firm* — Bacon & Thomas, PLLC

(57) ABSTRACT

Tool and method for creating a perforation or cavity in a bone or bone structure in contact with a membrane, the tool including a drill having a free end and a channel adapted for supplying a liquid under pressure to the free end, the tool further including a source of the liquid under pressure such that the liquid flows partially into and through the bone or bone structure toward the membrane while drilling the bone or bone structure with the drill, which allows to perform a progressive detachment of the membrane when the drill is close to the membrane while still being inside the bone or bone structure, and before completely piercing the bone or bone structure.

20 Claims, 6 Drawing Sheets

(56) References Cited

U.S. PATENT DOCUMENTS

| | | | |
|---|---|---|---|
| 7,510,397 | B2 | 3/2009 | Hochman |
| 7,632,280 | B2 * | 12/2009 | Hochman ................. 606/94 |
| 7,771,199 | B2 | 8/2010 | Hochman et al. |
| 2006/0084034 | A1 | 4/2006 | Hochman |
| 2006/0088601 | A1 | 4/2006 | Overby et al. |
| 2006/0172255 | A1 * | 8/2006 | Hochman et al. ............ 433/144 |
| 2008/0020349 | A1 | 1/2008 | Dricot |
| 2009/0258328 | A1 | 10/2009 | Chen |
| 2009/0259227 | A1 * | 10/2009 | Ahn ............................ 606/80 |
| 2010/0185200 | A1 | 7/2010 | Dricot |
| 2010/0324561 | A1 | 12/2010 | Watzek et al. |

FOREIGN PATENT DOCUMENTS

| | | |
|---|---|---|
| DE | 10322869 | 11/2004 |
| EP | 0515274 | 11/1992 |
| EP | 1269933 A2 * | 1/2003 |
| IE | 980671 A1 | 2/2000 |
| WO | 87/05521 A | 9/1987 |
| WO | 2006/089380 A1 | 8/2006 |
| WO | 2009000052 | 12/2008 |
| WO | 2009/062225 A2 | 5/2009 |

OTHER PUBLICATIONS

International Search Report in PCT/BE2007/000068, Jul. 9, 2008.
First Examination Report of EPO regarding European patent application No. 07763799.9, Dec. 27, 2010, with translation.
English Translation of p. 8, last paragraph of AT 504,780 published Aug. 15, 2008, cited in Search Report of EPO in EP 10191050.3 on Mar. 22, 2011.
Search Report of EPO regarding European application No. 10191050.3, Mar. 22, 2011.
Pommer, B, et al., "Gel-Pressure Technique for Flapless Transcrestal Maxillary Sinus Floor Elevation: A Preliminary Cadaveric Study of a New Surgical Technique", The International Journal of Oral & Maxillofacial Implants, 2009, vol. 24, No. 5, pp. 817-822.
Chen, L. et al., "An 8-Year Retrospective Study: 1,100 Patients Receiving 1,557 Implants Using the Minimally Invasive Hydraulic Sinus Condensing Technique", Innovations in Periodontics, Mar. 2005, vol. 76, No. 3, pp. 482-491.
Dentsply Friadent-2 Stepped Cylinder web page product description from Osseosource at http://osseosource.com/dental-implants/product_info.php?products_id=1959, copy downloaded and printed Nov. 1, 2010.
European Office Action for EP 10 191 050.3 dated Dec. 14, 2012.
European Office Action for EP 10 191 050.3 dated May 30, 2012.

* cited by examiner

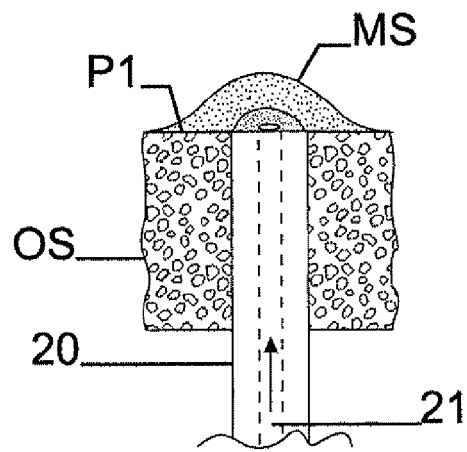
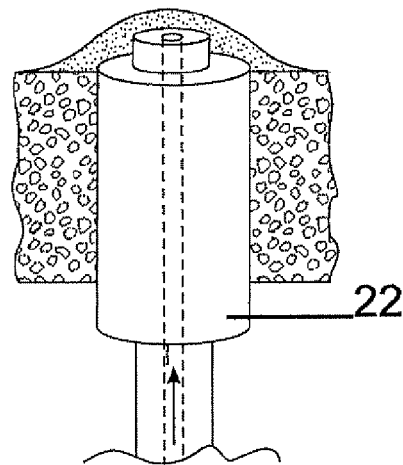
Fig. 2a                Fig. 2b
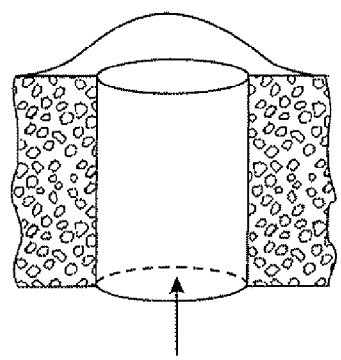
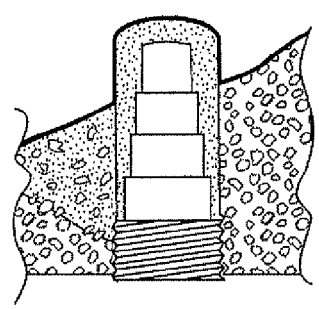
Fig. 2c                Fig. 2d

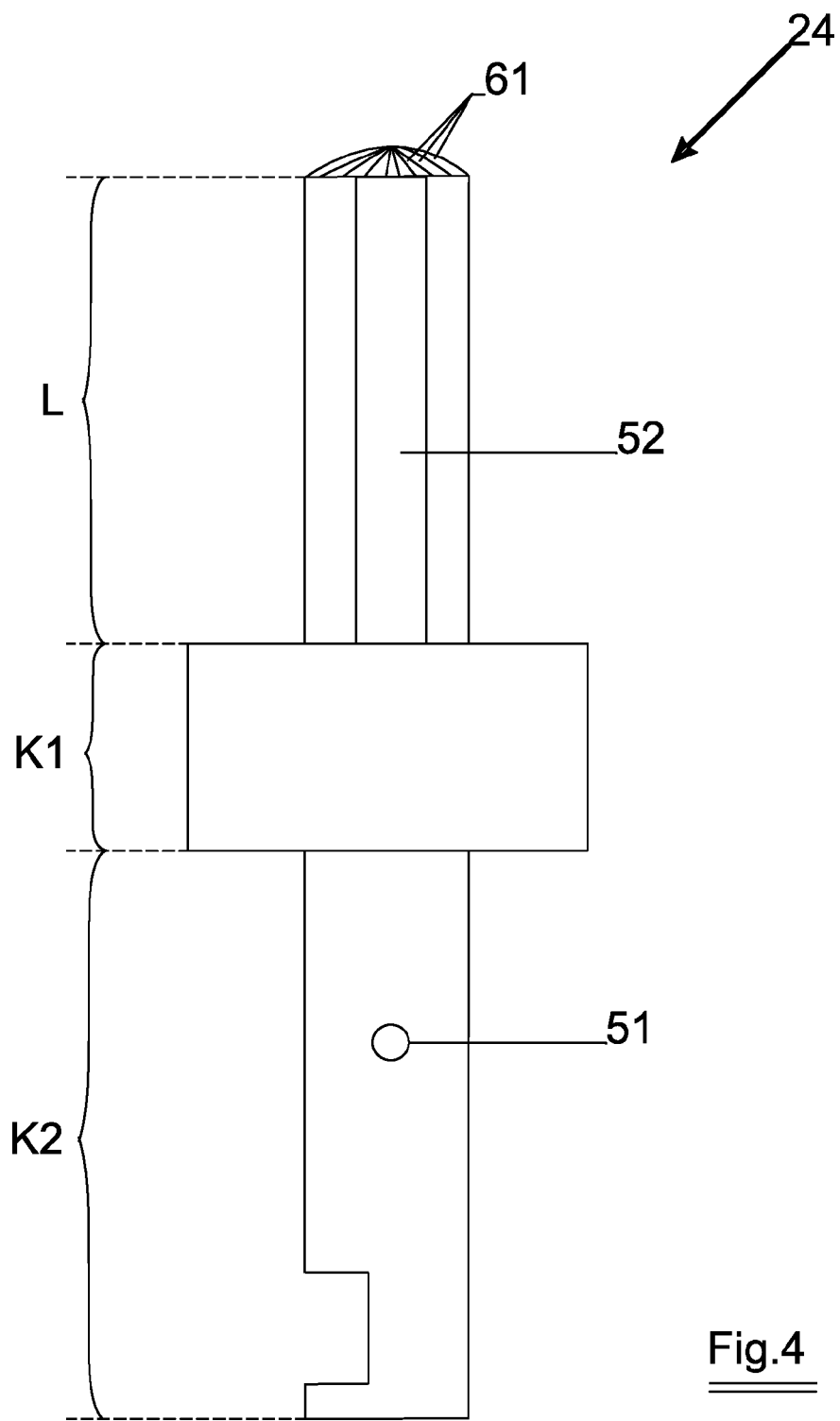

METHOD AND TOOL FOR CREATING A PERFORATION OR CAVITY IN A BONE OR BONE STRUCTURE IN CONTACT WITH A MEMBRANE

This application is a continuation-in-part of prior application Ser. No. 12/666,604 filed Dec. 23, 2009 (PCT/BE2007/000068 filed Jun. 27, 2007), the entire contents of which are incorporated herein by reference.

BACKGROUND TO THE INVENTION

The present invention relates to a tool and associated method for creating a perforation or cavity in a bone or bone structure in contact with a membrane, such as the sinus membrane. The perforation or cavity may be used to place an implant, particularly a dental implant.

Dental implants may be used to replace lost teeth. The body of dental implants is normally made of titanium. Dental implants are discussed in more detail in U.S. patent application Ser. No. 12/666,604 mentioned already above.

For the placement of an implant into the upper maxilla, the integrity of the sinus membrane (also known as the Schneider membrane) should be preserved while creating the perforation or cavity, and also afterwards. If, for the specific implant that is to be placed, the height of the alveolar crest is insufficient, the bone mass may be augmented by a sinus lift. The upper maxilla is then perforated, the sinus membrane is detached from the sinus floor and lifted, and bone grafting material is injected through the hole, so that this material is introduced in a pocket between the sinus floor and the raised sinus membrane. The injected bone grafting material is a structure capable of promoting the formation of bone around the implant. Finally, in the last phase, the implant is placed. During the complete process, perforating of the sinus membrane should be avoided.

A first known method to separate the sinus membrane from the sinus floor, and to lift the sinus membrane, uses a sinus lifting tool. Separation and lifting is then done mechanically.

Other known sinus lifting methods are those of Watzek and of Chen.

In Watzek's patent application WO 2009/062225, a surgical instrument is disclosed for introducing a flowable medium in the perforated upper maxilla for lifting the Schneider membrane from the sinus floor. First a set of special drills is used to perforate the upper maxilla; some drills have cutting and non-cutting portions in order to minimize the risk of perforating the Schneider membrane during drilling. Then, through the opening in the sinus floor, the flowable medium is introduced by the surgical instrument, to lift the Schneider membrane.

Watzek's patent application AT 504 780 discloses a drill having two portions: a peripheral, rotating portion that cuts, and a central portion. The central portion does not rotate and can move with respect to the peripheral portion in the axial direction of the drill. The central portion has at least one opening for a cooling fluid that cools the drill and the bone during the drilling operation. The cooling fluid also serves to remove the bone debris resulting from drilling. Near the end of the drilling phase, the central portion is moved forward in the axial direction, preferably by tapping, so that the small remaining portion of the sinus floor is broken off and is lifted by the central portion, together with the Schneider membrane.

Another technique is described in a publication by Pommer and Watzek, The International Journal of Oral & Maxillofacial Implants, p. 817-822, Vol. 24, Number 5, 2009. In this study, the sinus floor is punctured by a drill that has a rounded tip, in order to prevent perforating the sinus membrane, and a radiopaque gel is then injected through the puncture to separate and elevate the sinus membrane from the sinus floor.

Still another technique is disclosed in "An 8-Year Retrospective Study: 1,100 Patients Receiving 1,557 Implants Using the Minimally Invasive Hydraulic Sinus Condensing Technique", L. Chen and J. Cha, Journal of Periodontology, March 2005, Vol. 76, Number 3, p. 482-491. A hole is drilled in the alveolar crest, and drilling ceases about 1 mm short of the sinus floor. The surgeon then downsizes to a 2 mm sinus bur for the purpose of forming a narrow conical shape at the end of the hole. While rotating, the 2 mm sinus bur is gently tapped through the cortical bone of the sinus floor just hard enough to form a pinhole. At this stage, hydraulic pressure from the handpiece of the drill is introduced to the surgical site, providing enough force to begin dissecting the membrane from the sinus floor. Once the membrane is loosened, hydraulic pressure is ceased. The membrane is then at rest but slightly detached.

Chen's patent application US 2009/0258328 discloses a dental implant method and apparatus, wherein a dental implant may be placed during one surgery by extracting a tooth from a socket, drilling a hole through crestal bone at the top of the socket, dissecting sinus membrane from the crestal bone by pulsing water through the hole and separating the sinus membrane from the crestal bone, then inserting bone mixture through the hole and between the sinus membrane and the crestal bone to increase the thickness of crestal bone. A hydraulic dental instrument is provided that pulses water through the drilled hole and separates the sinus membrane from the crestal bone.

SUMMARY OF THE INVENTION

Applicant has found that when drilling a perforation or cavity in a bone or bone structure in contact with a membrane, the membrane can be progressively detached from the bone or bone structure, and this during the drilling operation, when the drill is close to the membrane while still inside the bone or bone structure, and before the bone or bone structure is completely pierced. The tool in accordance with the invention includes a drill having a free end and a channel adapted for supplying a liquid under pressure to the free end of the drill. The tool further includes a source of the liquid under pressure, such that the liquid flows partially into and through the bone or bone structure toward the membrane while drilling the bone or bone structure.

The pressure of the liquid supplied by the liquid source, and the liquid flow, are such that a portion of the supplied liquid passes through the bone to detach the membrane, while drilling. In case the concerned membrane is the sinus membrane, a pocket of liquid is then formed between the sinus floor and the sinus membrane before the drill reaches the sinus floor. Thus, when the drill pierces the sinus floor, the sinus membrane was already lifted and hence cannot be perforated by the drill; moreover the pocket of liquid protects the membrane against the drill.

This tool and the corresponding method are disclosed in application Ser. No. 12/666,604, mentioned already above. The progressive detachment of the sinus membrane is based on hydraulic, not on mechanical principles. The bone of the alveolar crest is porous to the supplied liquid, whereas other types of bone are not, as discussed further below; moreover, the sinus membrane is impermeable to the liquid. This is shown by the use of a tool according to the invention, whereby a pocket of liquid is formed below the sinus membrane. The disclosed method, and further improvements set out below, were applied for 27 sinus lifts on patients since October 2005 (the patients did not see or know how the invention worked nor what its constitution was). All performed sinus lifts were successful, i.e. the success rate is 100%.

An improved embodiment in accordance with the invention includes a flow adapter for diverting a portion of the liquid that enters the channel of the drill. The remaining flow of liquid at the free end of the drill is thus smaller (or at most equal, if the diverted portion is zero) than the flow of liquid entering the channel. The flow of liquid at the free end can thus be adapted to the drilling conditions (such as the bone height), so that an appropriate flow of liquid enters the bone. In one embodiment, an open space is present in the channel of the drill, between an insert into the channel and the inner wall of the channel, so that the diverted flow flows back into this open space, in the direction opposite to that of the incoming liquid in the insert.

The method according to the invention has numerous advantages. The most important advantage is that since the sinus membrane is detached before the sinus floor is pierced by the drill, and since a pocket of liquid is formed under the membrane, there is no risk of perforating the sinus membrane. Moreover, the sinus membrane is progressively detached, so that there is no risk of damaging the membrane, in contrast to prior art methods where the detachment is done abruptly. Further, the sinus lift and placement of the implant take very little time (about half an hour) and the entire intervention is a one step process, if the alveolar crest is high enough (e.g. 3 mm or more) to guarantee good stability of the placed implant; otherwise, the implant is placed at a later stage.

The tool and method according to the invention can also be used when drilling a bone or bone structure in contact with another membrane than the sinus membrane, as will become clear from the detailed description below.

The invention also includes a kit of drills adapted to perform the method according to the invention.

BRIEF DESCRIPTION OF THE DRAWINGS

Embodiments of the invention will be described, by way of example only, with reference to the accompanying drawings in which:

FIGS. 2a through 2d schematically illustrate steps for the drilling of a hole according to the invention, followed by the installation of an implant;

FIGS. 3 to 5 illustrate embodiments of drills in accordance with the invention;

DETAILED DESCRIPTION OF PREFERRED EMBODIMENTS

FIGS. 1 and 2a to 2d illustrate a first embodiment in accordance with the invention.

Figure 1:
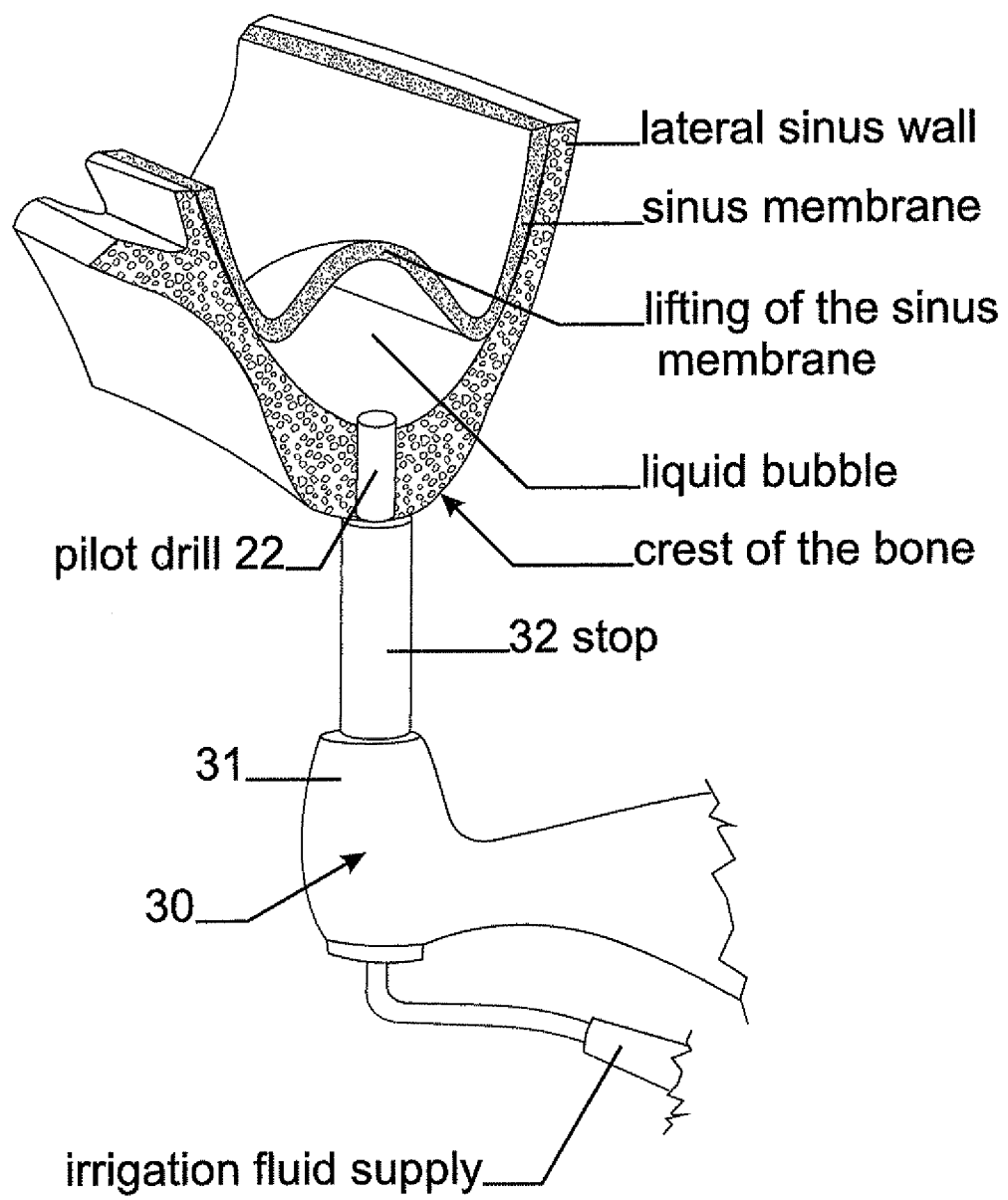
FIG. 1 is a schematic view of a tool according to the invention.

FIG. 1 is a schematic perspective view of a perforation device that carries a drill 22. The device comprises a support 30 whose head 31 is equipped with a means for driving the drill 22 in rotation. The head 31 is associated with a stop 32 whose position is advantageously adaptable as a function of the length of the movement for piercing the bone with the guide drill. The irrigation system of this tool makes it possible to detach the Schneider membrane before the tool pierces the sinus floor, thanks to the delivery of a liquid under pressure to the free end of the drill 22 during drilling. The pressure is advantageously capable of passing the liquid through at least a portion of the bone.

FIGS. 2a through 2d schematically illustrate steps for the installation of an implant. The bone structure (OS) is drilled with a drill 20 having a central channel 21 for supplying a liquid under pressure. Because of the porosity of the bone structure, the liquid under pressure in the channel flows partially into the bone. The closer the free end of the guide drill comes to the inner bone wall P1, e.g. the sinus floor, the easier the liquid under pressure flows into the bone toward the sinus membrane MS, thus making it possible, when the tool is close to the membrane (while still being inside the bone) to perform a progressive detachment of the sinus membrane MS, before the drill 20 pierces the bone structure OS, since a pocket of liquid (called liquid bubble in FIG. 1) is formed between the sinus floor and the membrane.

Besides detaching the sinus membrane, and forming a pocket of liquid, another function of the liquid is to cool the drill and the bone during drilling.

Instead of a drill 20, 22, in a less preferred embodiment a sonic or ultrasonic cavitation tool is used. Also during the operation for piercing a hole by ultrasonic cavitation, a liquid under pressure is supplied through an inner channel of the cavitation tool.

The pressurization of the liquid may or may not be continuous, for example, occurring in successive stages. For example, the liquid may be subjected to a pressurization cycle comprising high pressure stages and low- or average- and/or no-pressure stages.

In one embodiment, when the drill comes close to the membrane, a drop in pressure is detected. This pressure drop makes it possible to warn the practitioner that the bone structure OS will soon be pierced. This signal may be used to trigger an injection or control an injection of a precise volume of liquid in order to ensure an adequate detachment of the sinus membrane. For example, once the pressure drop signal is detected, a volume of 5 ml of aseptic liquid (water) is injected. When the 5 ml of liquid are injected, the rotation of the guide drill is interrupted.

After the bone is pierced completely, a hole of larger diameter is drilled along the guide drill by means of one or more drills 22. During the complementary drilling along the guide drill to increase the diameter of the hole, it may be appropriate to check the pressure of liquid in the channel 21 of the guide drill. For example, as soon as this pressure falls below a given level, a control device re-supplies water under pressure to ensure that the sinus membrane is still properly detached and separated from the bone structure near the location of the hole to be drilled.

When the hole has a diameter that substantially corresponds to the diameter of the implant, the drill and the guide drill are withdrawn. A bone grafting composition is then injected through the hole and the implant is then inserted (FIG. 2d).

The liquid that is used in embodiments according to the invention is preferably a normal saline solution (sometimes called physiological saline solution). It may also e.g. be water, an isotonic saline solution, a solution of water containing from 0.5% by weight to 3% by weight of NaCl, for example from 0.7 to 1.5% by weight of NaCl. A radiopaque product may be added to the liquid in order to follow the detachment and lifting of the membrane in real time. The liquid is pressurized, either continuously or otherwise.

When the liquid is pressurized, part of the liquid passes into the porous structure of the bone. The alveolar crest consists mainly of bone mass of type III and IV, which are porous to the liquid. The bone structures (of the palate and the skull) that support the alveolar crest however belong to bone mass of type I, and are impermeable to the liquid.

It has been shown that there is no risk that the liquid passes to other anatomical structures than the alveolar crest; the liquid forms a pocket below the Schneider membrane, and does not pass e.g. to the soft tissues of the face. The liquid is totally harmless for the bone structure; necrosis of the alveolar crest was never seen after an intervention in accordance with the invention.

Figure 3A:
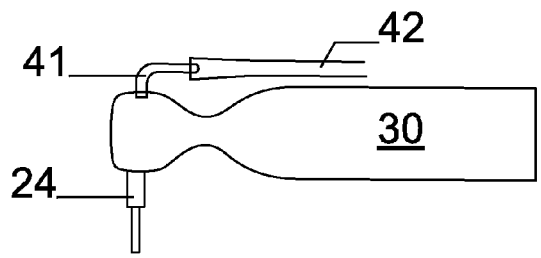
Figure 3B:
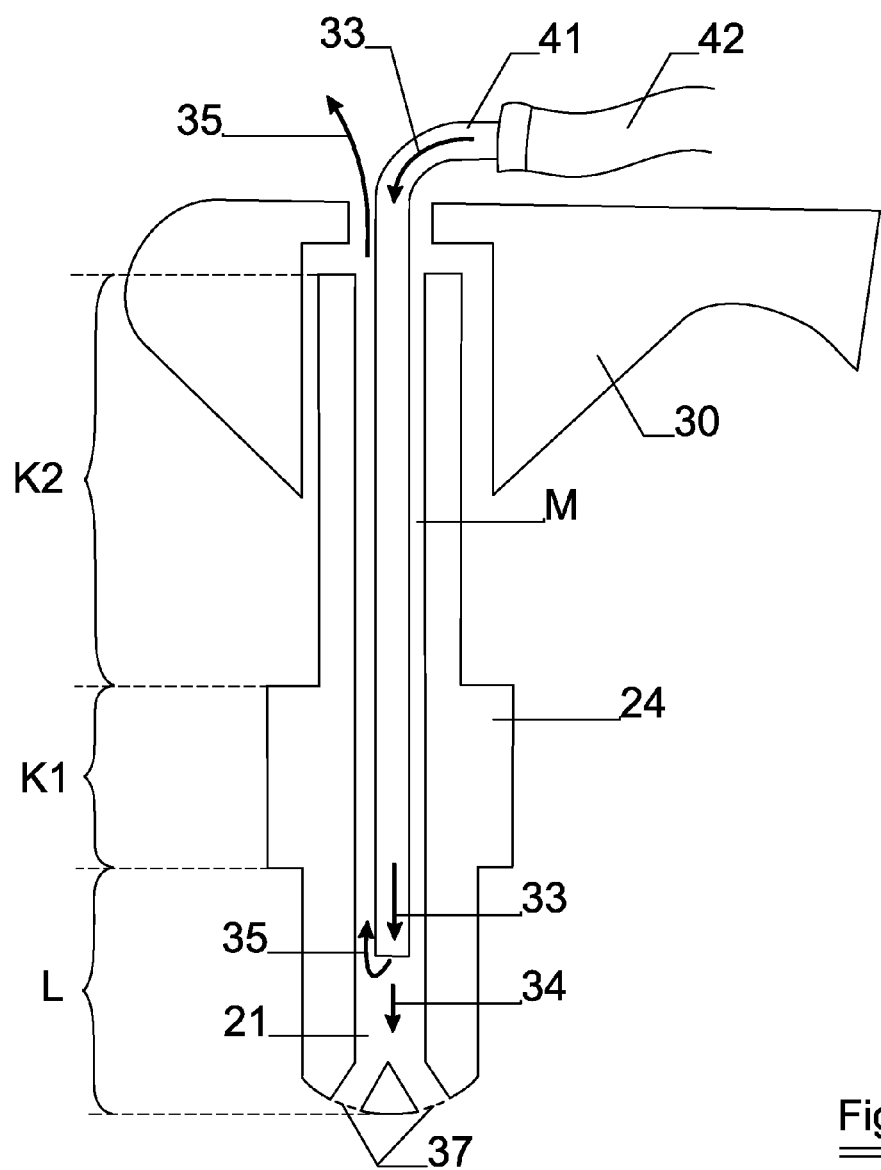
Figure 5:
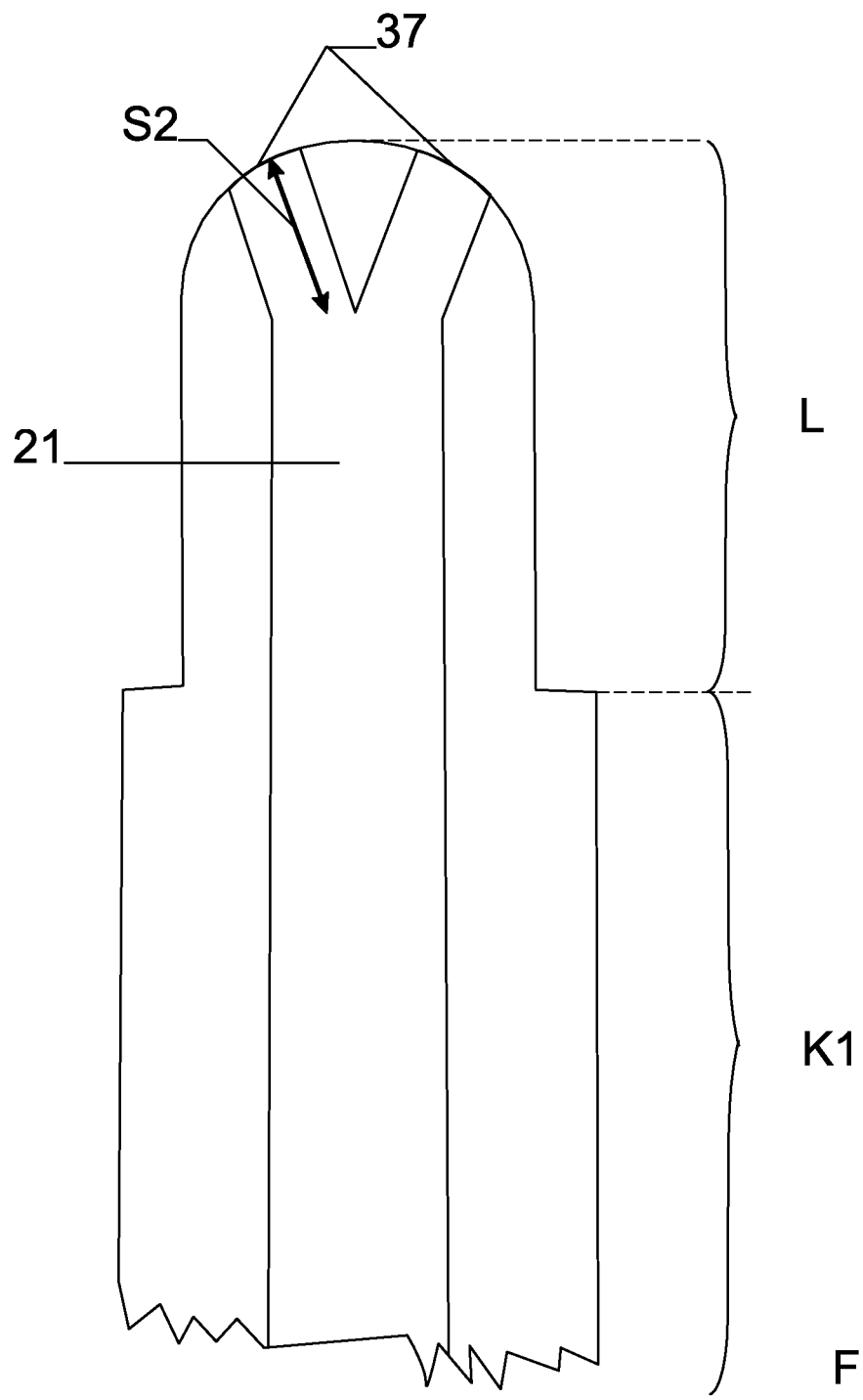

FIGS. 3a and 3b show a particular embodiment of the invention that includes a flow adapter, as will now be explained. FIG. 3a shows a drill 24 mounted in a support 30. Pressurized liquid from a pump (not shown) flows through a tube 42 to an insert 41 in the channel of drill 24. The pumps used for this kind of interventions usually supply a constant liquid flow, independent of the rotational speed of the drill. The drill 24 is shown schematically in more detail in FIG. 3b (in order to keep the drawing clear, parts such as e.g. the driving mechanism of the drill and the mounting of the insert are not shown). The outer diameter of the insert 41 is smaller than the inner diameter of the channel 21, so that an open space M is created between the inner wall of the channel and the insert. The pump supplies a flow 33 of liquid to the insert. Flow 33 streams from the insert into the channel 21, but it does not completely stream out of the openings 37 at the free end of the drill. Because of the pressure of the liquid in the drilled cavity, a portion of the liquid flows back through the open space M: liquid flow 33 is split into flow 34 and flow 35. Flow 34 is supplied to the free end of the drill and flow 35 flows back through the open space M and through the support 30 (and may e.g. end up on the floor, which is not a problem since the amount of liquid is quite small). How much liquid is supplied through the channel to the free end depends on the size of the open space M and on the pressure of the liquid outside of the free end and in the drilled cavity; if this pressure is higher, the backflow 35 of liquid will be larger, and less liquid 34 will be supplied to the free end.

This backflow system is very useful. It avoids that the pressure inside the bone structure becomes too high, which could be harmful for the bone tissue (a high pressure could occur if a large liquid flow would pass through a large bone height). It also avoids that, for large bone heights, a too large liquid pocket would be formed under the sinus membrane, which would "drown" the sinus. Applicant has found that a liquid pocket having a volume of about 1 to 3 ml is sufficient.

The backflow system discussed above is just one embodiment of a flow adapter diverting a portion of the liquid after entering the channel of the drill, such that the flow of liquid supplied to the free end of the drill is smaller than the flow of liquid entering the channel. Such a flow adapter modulates, or adapts, the flow of liquid and its pressure during the drilling operation, depending on the drilling conditions (such as the bone height). An important parameter of the backflow system is the size of the open space M; this is discussed more in detail further below.

The drill 24 shown in the embodiment of FIG. 3b has three segments, L, K1 and K2. Segment K1 is a stop; it determines the working length L of the drill. When the stop K1 touches the bone, drilling with this drill is stopped. Preferably the diameter of segment K1 is about 2 mm larger than the diameter of segment L. Segment L includes cutting elements near the free end, such as cutting edges (shown in FIG. 4, cutting edges 61), cutting elements including diamond powder, or other cutting elements as known in the art. The outer surface of segment L is preferably smooth, i.e. non-cutting. Segment K2 is the portion of the drill behind the stop.

FIG. 4 shows an embodiment of a drill comprising a transverse opening 51 that connects the channel 21 of the drill to the outside surface of the drill. A drill may comprise no, one, or a plurality of transverse openings 51. These transverse openings evacuate liquid from the channel, and also modulate the flow of liquid supplied to the free end of the drill. They also affect the liquid pressure at the free end. They are also an embodiment of the flow adapter discussed above. Transverse openings may pierce the outer surface of the drill perpendicular to its axis, or inclined under an angle. Preferably, they are located in segment K2 or in segment K1 of the drill. A transverse opening may have a circular shape, an oval shape, or another shape. Circular transverse openings preferably have a diameter between 0.1 and 3 mm.

Figure 7A:
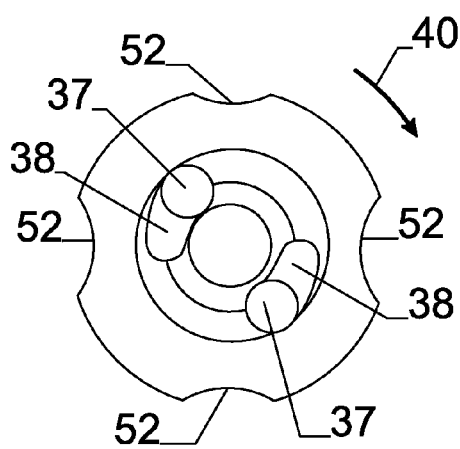

A drill may also comprise one or more drainage gutters 52, shown in FIGS. 4 and 7a, in segment L of the drill. They help to evacuate liquid from the free end of the drill, and also to evacuate bone debris. They also affect the liquid pressure at the free end, and the flow of liquid into and through the bone.

A drill may comprise any combination of the features transverse openings, drainage gutters, and backflow; i.e. only backflow may be present, or backflow and one or more transverse openings, or backflow and transverse openings and drainage gutters; only drainage gutters may be present, etc.

A drill may have one opening 37 at its free end through which the liquid of the channel 21 is supplied to the cavity, the drill may have two openings 37, four openings . . . . Different embodiments are shown in FIGS. 5 to 8. If there are two or more openings, channel 21 is split into subchannels; the length of these subchannels, S2 (see FIG. 5), is preferably less than 15 mm.

Figure 6A:
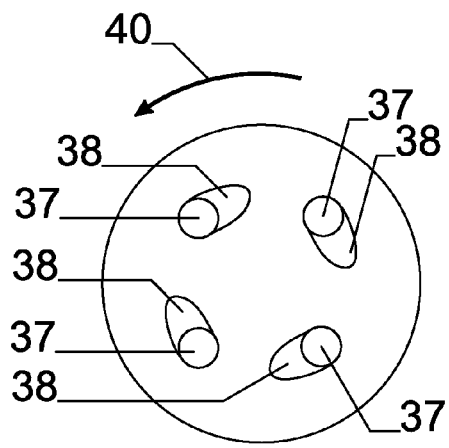
FIGS. 6 to 8 illustrate portions of drills according to the invention.
Figure 6B:
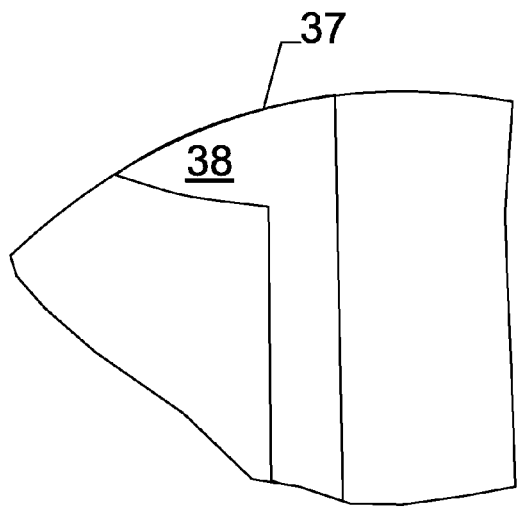
Figure 7B:
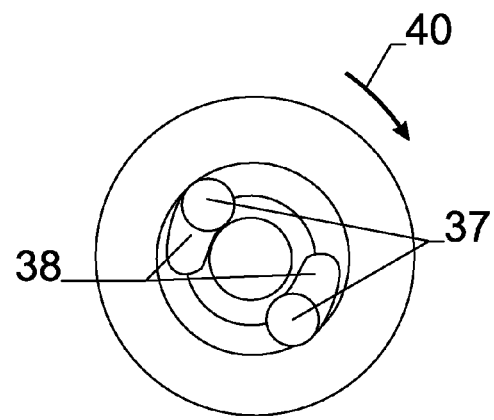
Figure 8:
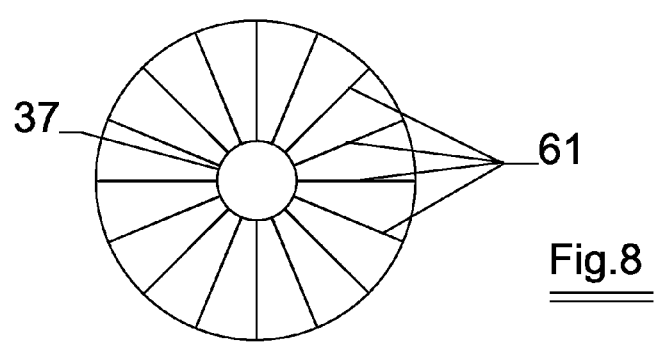

In order to prevent that an opening 37 of the drill gets blocked, e.g. by bone debris, the drill may comprise an anti-blocking gutter 38 at its free end. FIGS. 6 to 8 show different embodiments. In FIG. 8, where the drill has only one opening, no anti-blocking gutter is present (the opening may be cleaned regularly by the practitioner). The anti-blocking gutters 38 are preferably located, with respect to the corresponding opening 37, in the direction opposite to the rotation direction 40 of the drill. The anti-blocking gutters also allow easier cleaning of the openings.

Referring now again to FIG. 3b, an important parameter of the backflow system is the size of the open space M, which is determined by the difference in diameter between the channel 21 and the insert 41. If the open space M is larger, the backflow will be larger. Less liquid will then enter the bone or bone structure, and the pressure at the free end of the drill will be reduced. As is explained further below, the invention allows to adapt the pressure and the flow of liquid supplied at the free end to the drilling conditions, such as the drilling depth. In this way, too high pressures and "drowning" of the sinus are avoided, and an optimal detachment of the sinus membrane is obtained. An optimal detachment includes that the membrane is detached over not too large an area. An optimal detachment area is about 1 to 3 $cm^2$; the optimal amount of liquid in the pocket under the membrane is about 1 to 3 $cm^3$.

To obtain these results, it is advantageous to use a kit of drills in accordance with the invention, that contains drills that have to be used in the correct order. Preferably, the kit of drills that is used in case the height of the alveolar crest is larger than about 3 mm is different from the kit of drills for alveolar crests with a height smaller than about 3 mm. The drills of the kits have characteristics that are optimized for the drilling depth at which they are used.

First, a preferred embodiment of a kit of drills for an alveolar crest higher than about 3 mm is discussed. Initially, the practitioner uses a first drill optimized for a first drilling depth; then he uses a second drill optimized for a second drilling depth, deeper than the first one; he then possibly uses a third drill to drill even deeper, and so on. The drilling depths of the drills are preferably defined by the location of their stops K1. An important parameter that is optimized is the size of the open space M, which determines the backflow. For a drill working at a depth of e.g. 7 mm, the optimal backflow may be as large as 90%, whereas the backflow is only about 10 to 30% for a drill having a maximum drilling length of 3 to 4 mm, for example. To obtain a higher backflow for a drill for a larger drilling depth, the inner diameter of the channel 21 may be enlarged, since the outer diameter of the insert 41 is usually constant. Thus, in the preferred embodiment of the kit, the second drill, optimized for a second drilling depth deeper than the first drilling depth of the first drill, has a channel 21 with a larger inner diameter than that of the first drill. In the preferred embodiment of the kit, the inner diameter of the channel 21 increases for drills optimized for deeper and deeper drilling depths. In this way, the backflow is increased. Further, when using a drill for a deeper drilling depth, the diameter of the cavity, and thus the diameter of the drill, may be increased.

In case the height of the alveolar crest is smaller than about 3 mm, the kit of drills is preferably different. Here, it is important to have a large liquid flow into and through the bone, in order to have an optimal detachment of the sinus membrane. The backflow is e.g. 10 to 20% in this case, or even 0 to 10%. Therefore, the diameter difference between the channel 21 and the insert 41 is very small, or even zero (of course the drill 24, which is only shown schematically in FIG. 3b, may have non-rotating stationary parts, e.g. the part in contact or nearly in contact with the insert 41, in this ease). Preferably, the drills of this kit have no drainage gutters. It is further preferred that they do not have transverse openings. In one embodiment, the first drill has a diameter of about 2.5 mm and the second drill has a diameter of about 3.3 mm. In another embodiment, the first drill has a diameter of 3.3 mm. Further, the opening or openings 37 in the free end are preferably as centered as possible. Because of the small bone height, the drills advantageously advance slowly in the bone, so that enough liquid can pass through the bone to the sinus membrane. This may be achieved e.g. by using cutting elements with fine diamond powder or with cutting edges that are little abrasive.

In the kits in accordance with the invention, the drills preferably have diameters between 1 and 6 mm. The length of section K1 is preferably between 1 and 15 mm. The size of the open space M is preferably less than 3 mm.

It is important to use a kit of drills having dimensions with tight tolerances, in order to obtain an optimal result.

I claim:

1. A tool for creating a perforation or cavity in a bone or bone structure in contact with a sinus membrane, said tool comprising:
   a drill having a first end for connection with a handpiece, a second free end, and a channel extending along the axis of said drill from said first end to said second free end, said channel including at least one opening at the drill second free end that is at an angle to the longitudinal axis of the drill for supplying a liquid under pressure to said second free end, wherein the liquid is a solution of water containing from 0.5% by weight to 3% by weight of NaCl,
   said tool further comprising an insert configured to be inserted into said channel of said drill, said insert having a first end connected to a source of said liquid under pressure, thus enabling supply of said liquid to said channel, and defining a first flow path for said liquid to flow through said insert to said channel and a second end located inside the channel remote from said at least one opening at the second free end of the drill,
   wherein an outer diameter of said insert is smaller than an inner diameter of said channel to create an open space between said insert and said channel, said open space having an exit defining a second flow path for a backflow of said liquid to flow through said open space in a direction opposite to a direction of a flow of said liquid flowing along said first flow path, and
   wherein said insert and said at least one opening at the second free end define a third flow path for said liquid to flow from said insert to said at least one opening at the second free end;
   wherein said first, said second, and said third flow paths are configured such that, while drilling the bone or bone structure with the drill, said liquid flowing along said first flow path is split inside said channel at a split location between the second end of the insert and the at least one opening at the second free end of the drill into said liquid flowing along said second flow path and said liquid flowing along said third flow path,
   so that said liquid is partially flowable into and through the bone or bone structure toward the sinus membrane, thereby enabling performance of a progressive detachment of the sinus membrane when the drill is close to the sinus membrane while still being inside the bone or bone structure, and before completely piercing the bone or bone structure.

2. Tool according to claim 1 wherein said drill has an outside surface including a drainage gutter for liquid evacuation.

3. Tool according to according claim 1 wherein said drill comprises a transverse opening connecting said channel to an outside surface of said drill, for liquid evacuation.

4. Tool according to according to claim 1 wherein said drill comprises an anti-blocking gutter at its second free end preventing said second free end from being blocked when drilling said bone or bone structure.

5. Tool according to claim 1 wherein said drill comprises a plurality of openings for said liquid at said second free end.

6. Tool according to claim 1 wherein said second free end of said drill comprises a cutting element.

7. Tool according to claim 1 wherein said drill comprises a stop.

8. The tool according to claim 1, wherein said liquid flowing along said first flow path is split at a split location inside said drill into said liquid flowing along said second flow path and said liquid flowing along said third flow path and wherein said first, said second and said third flow paths are configured such that at said split location said liquid flowing by said first flow path is flowing in a first direction, said liquid flowing by said second flow path is flowing in a second direction opposite to said first direction and said liquid flowing by said third flow path is flowing in said first direction.

9. An insert and drill kit for creating a perforation or cavity in a bone or bone structure in contact with a sinus membrane, said insert and drill kit comprising:
   at least one drill, each drill of said insert and drill kit having a first end for connection with a handpiece, a second free end, and a channel extending along the axis of said drill from said first end to said second free end, said channel including at least one opening at the drill second free end that is at an angle to the longitudinal axis of the drill adapted for supplying a liquid under pressure through said channel to said second free end, wherein the liquid is a solution of water containing from 0.5% by weight to 3% by weight of NaCl, an insert being configured to be inserted into said channel, said insert having a first end connectable to source of said liquid under pressure thereby enabling supply of said liquid to said channel, and defining a first flow path for said liquid to flow through said insert to said channel and a second end located inside the channel remote from said at least one opening at the second free end of the drill, wherein said insert has an outer insert diameter and said channel has an inner channel diameter, wherein, for each said drill of said insert and drill kit, said inner channel diameter is larger than said outer insert diameter to create an open space between said insert and said channel, said open space having an exit defining a second flow path for a backflow of said liquid to flow through said open space in a direction opposite to a direction of a flow of said liquid flowing along said first flow path, and wherein said insert and said at least one opening at the second free end define a third flow path for said liquid to flow from said insert to said at least one opening at the second free end;

wherein, for each drill of said insert and drill kit, said first, said second, and said third flow paths are configured such that, while drilling the bone or bone structure with the drill, said liquid flowing along said first flow path is split inside said channel at a split location between the second end of the insert and the at least one opening at the second free end of the drill into said liquid flowing along said second flow path and said liquid flowing along said third flow path.

10. Tool according to claim 9, wherein said drill has an outside surface including a drainage gutter for liquid evacuation.

11. Tool according to claim 9, wherein said drill comprises a transverse opening connecting said channel to an outside surface of said drill, for liquid evacuation.

12. Tool according to claim 9, wherein said drill comprises an anti-blocking gutter at its second free end for preventing said second free end from being blocked when drilling said bone or bone structure.

13. Tool according to claim 9, wherein said drill comprises a plurality of openings for said liquid at said second free end.

14. Tool according to claim 9, wherein said second free end of said drill comprises a cutting element.

15. Tool according to claim 9, wherein said drill comprises a stop.

16. The insert and drill kit according to claim 9 wherein, for each drill of said insert and drill kit, said first, said second and said third flow paths are configured such that said liquid flowing along said first flow path is split at a split location inside said drill into said liquid flowing along said second flow path and said liquid flowing along said third flow path and wherein said first, said second and said third flow paths are configured such that at said split location said liquid flowing by said first flow path is flowing in a first direction, said liquid flowing by said second flow path is flowing in a second direction opposite to said first direction and said liquid flowing by said third flow path is flowing in said first direction.

17. A method for creating a perforation or cavity in a bone or bone structure in contact with a sinus membrane, said method comprising:

drilling said bone or bone structure with a drill having a first end for connection with a handpiece, a second free end, and a channel extending along the axis of said drill from said first end to said second free end, said channel including at least one opening at the drill second free end that is at an angle to the longitudinal axis of the drill for supplying a liquid under pressure to said second free end;

supplying a liquid under pressure along a first flow path through an insert in a channel of said drill, said insert having a first end connected to a source of said liquid under pressure, and a second end located inside the channel remote from said at least one opening at the second free end of the drill, wherein the liquid is a solution of water containing from 0.5% by weight to 3% by weight of NaCl;

splitting said supplied liquid inside said channel at a split location between the second end of the insert and the at least one opening at the second free end of the drill into a portion of said liquid and another portion of said liquid;

supplying said portion of said liquid along a second flow path through an open space between an inner surface of said channel and an outer surface of said insert to an exit of said open space;

enabling said portion of said liquid to flow back through said open space in a direction opposite to a direction of flow of said supplied liquid;

supplying said another portion of said liquid along a third flow path from said insert to the at least one opening at the second free end of said drill thereby enabling said liquid to flow partially into and through the bone or bone structure toward the sinus membrane while drilling the bone or bone structure with the drill, thereby enabling performance of a progressive detachment of the sinus membrane when the drill is close to the sinus membrane while still being inside the bone or bone structure, and before completely piercing the bone or bone structure.

18. Method according to claim 17 further comprising:

drilling said bone or bone structure until a stop of said drill contacts said bone or bone structure, thereby defining a first drilling depth; and subsequently further drilling said bone or bone structure by a second drill until a second stop of said second drill contacts said bone or bone structure, thereby defining a second drilling depth deeper than said first drilling depth.

19. The method according to claim 17, further comprising:

enabling, at said split location, said liquid flowing by said first flow path to flow in a first direction, said liquid flowing by said second flow path to flow in a second direction opposite to said first direction and said liquid flowing by said third flow path to flow in said first direction.

20. The method according to claim 19 further comprising:

drilling said bone or bone structure until a stop of said drill contacts said bone or bone structure, thus drilling up to a first drilling depth; and subsequently further drilling said bone or bone structure by a second drill until a second stop of said second drill contacts said bone or bone structure, thereby defining a second drilling depth deeper than said first drilling depth.

* * * * *